United States Patent [19]

Lin et al.

[11] Patent Number: 5,834,544
[45] Date of Patent: Nov. 10, 1998

[54] ORGANIC MATERIALS STABILIZED BY COMPOUNDS CONTAINING BOTH AMINE AND HINDERED PHENOL FUNCTIONAL FUNCTIONALITIES

[75] Inventors: Chung-Yuan Lin, Orange; R. Scott Archibald, Waterbury, both of Conn.

[73] Assignee: Uniroyal Chemical Company, Inc., Middlebury, Conn.

[21] Appl. No.: 954,773

[22] Filed: Oct. 20, 1997

[51] Int. Cl.⁶ .............. C08K 5/20; C08K 5/36; C08K 5/48; C07C 233/00
[52] U.S. Cl. .............. 524/217; 524/222; 564/155; 564/156
[58] Field of Search .............. 524/217, 222; 564/155, 156

[56] References Cited

U.S. PATENT DOCUMENTS

| | | | |
|---|---|---|---|
| 2,562,802 | 7/1951 | Mankiwich et al. | 260/576 |
| 3,304,283 | 2/1967 | Hawkins et al. | 260/45.9 |
| 3,432,578 | 3/1969 | Martin | 260/880 |
| 3,452,056 | 6/1969 | Sundholm | 260/390 |
| 3,505,225 | 4/1970 | Wheeler | 252/33.6 |
| 3,567,664 | 3/1971 | Haring | 260/2.5 |
| 3,637,865 | 1/1972 | Haring | 260/611.5 |
| 3,644,482 | 2/1972 | Dexter et al. | 260/473 R |
| 3,655,559 | 4/1972 | Holt | 252/51.5 A |
| 3,979,180 | 9/1976 | Lorand | 260/23 H |
| 3,988,363 | 10/1976 | Spivack et al. | 524/222 |
| 4,007,230 | 2/1977 | Hinze | 260/611.5 |
| 4,093,587 | 6/1978 | Spivack | 524/222 |
| 4,341,677 | 7/1982 | Tamosauskas | 523/421 |
| 4,420,579 | 12/1983 | Braid | 524/328 |
| 4,440,671 | 4/1984 | Turbett | 252/573 |
| 4,797,511 | 1/1989 | Capolupo et al. | 174/110 PM |
| 4,837,259 | 6/1989 | Chucta | 524/258 |
| 5,047,530 | 9/1991 | Wheeler et al. | 544/197 |
| 5,120,844 | 6/1992 | Wheeler et al. | 544/209 |

FOREIGN PATENT DOCUMENTS 59-98148  6/1984  Japan.

OTHER PUBLICATIONS

Nirula, S.C., *Antioxidants*, (Menlo Park, CA: Process Economics Porgram, 1983), Rpt. 85A.

Pospisil, J., *Mechanisms of Aromatic Amine Antidegradants*, Polymer Stabilization and Degradation, (American Chemical Society, 1985) 157–172.

Pospisil, J., *Aromatic Amine Atidegradants*, Developments in Polymer Stabilisation–7, Scott, G., ed., 1984, 44–47, 56–57, 60–61.

Shelton, J.R., *Organic Sulphur Compounds and Preventive Antioidants*, Developments in Polymer Stabilisation–4, Scott, G., ed. (London, UK: Applied Science Publishers Ltd, 1981), 58–63.

Primary Examiner—Kriellion S. Morgan
Attorney, Agent, or Firm—Raymond D. Thompson; Paul Grandinetti

[57] ABSTRACT

The present invention relates to compounds containing dual substitutions of an aromatic amine and hindered phenol functionality useful as stabilizers for organic materials. These compounds are of the general formula:

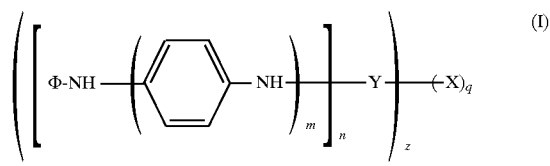

wherein:

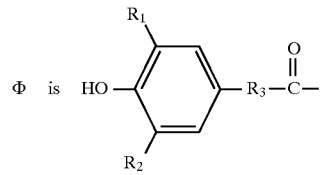

$R_1$ and $R_2$ are independently selected from the group consisting of hydrogen, substituted or unsubstituted aryl, and substituted or unsubstituted alkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1.

33 Claims, No Drawings

ORGANIC MATERIALS STABILIZED BY COMPOUNDS CONTAINING BOTH AMINE AND HINDERED PHENOL FUNCTIONAL FUNCTIONALITIES

BACKGROUND OF THE INVENTION

1. Field of the Invention

This invention relates to the protection of organic materials, such as rubber, plastic, lubricating oils, petroleum fuels, waxes, and organic liquids, from oxidation by the use of stabilizing compounds containing both amine and hindered phenol functionalities.

2. Description of Related Art

Organic materials such as rubber, plastic, lubricating oils, petroleum fuels, waxes, and organic liquids are well known to need protection from oxidation.

Currently, many of these organic materials are being exposed to higher operating temperatures and mechanical shear. New stabilizers that can protect organic materials from premature oxidation and degradation under these advanced operating conditions are being sought.

Hindered phenols have been used as stabilizers in organic materials such as food stuffs, rubber, plastics, oils, etc., for over 50 years. For example, U.S. Pat. No. 3,644,482 describes hindered phenol stabilizers based on esters of 3-(3,5-di-t-butyl-4-hydroxyphenyl)propionate.

In addition, aromatic amines have also been used as stabilizers of organic materials, especially for use in plastic, rubber, and oils. For example, U.S. Pat. No. 3,505,225 describes aromatic amine antioxidants based on α-methylstyryl-substituted diphenylamines. In addition, U.S. Pat. Nos. 4,797,511 and 4,837,259 describe the synergistic blends of hindered phenols and amine antioxidants as stabilizers for polypropylene and polyethylene.

Aralkyl-substituted diarylamines, such as 4,4'-bis(α, α-dimethylbenzyl)diphenylamine (NAUGARD 445, Uniroyal Chemical), and their use as antioxidants for a variety of polymeric materials are known from U.S. Pat. Nos. 3,452,056 and 3,505,225.

Sterically hindered phenols constitute another known class of antioxidant materials. Antioxidant compositions containing mixtures of an amine component and a sterically hindered phenol component, with and without other ingredients, are also known.

Thus, U.S. Pat. No. 3,304,283 discloses an antioxidant composition for mono-olefinic polymers, such as polypropylene, containing at least one aromatic phenolic thioether, diaryl thioether, aliphatic disulfide, aromatic disulfide, aromatic mercaptan, aliphatic mercaptan, and/or aliphatic thiuramdisulfide in combination with at least one biphenol and/or aromatic amine.

U.S. Pat. No. 3,432,578 discloses the stabilization of conjugated diene polymers from the adverse effects of ultraviolet radiation employing a mixture of a diaryl hydroxyamine, 2,6-di-t-butyl-4-methyl phenol, 1,3,5-trimethyl-2,4,6-tris (3,5-di-t-butyl-4 hydroxybenzyl) benzene, dilaurylthiodipropionate, and lignin sulfonate.

U.S. Pat. Nos. 3,567,664 and 3,637,865 both describe the stabilization of polyether polyol-based polyurethanes against scorching employing a mixture of 2,6-di-t-butyl-4-methyl phenol and a p,p'-dialkyl diphenylamine. Similarly, U.S. Pat. No. 4,007,230 describes the stabilization of polyether polyol-based polyurethanes against scorching employing a composition consisting of certain hindered phenols such as 2,4-di-methyl-6-octyl phenol and NAUGARD 445, referred to above.

U.S. Pat. No. 3,644,482 discloses esters derived from (4-hydroxy-5-alkylphenyl)-alkanoic acids, optionally substituted in the 2- or 3-position of the phenyl ring by a second alkyl group, and alkane polyols that are stabilizers of organic material normally subject to oxidative deterioration. They are prepared by conventional esterification techniques. Typical embodiments are ethylene glycol bis[3-(3.5-di-t-butyl-4-hydroxyphenyl)propionate] and pentaerythritol tetrakis [3-(3,5-di-t-butyl-4-hydroxyphenyl)propionate].

U.S. Pat. No. 3,655,559 discloses stabilizers for synthetic lubricants based on alkylated diphenylamines and, optionally, any one of numerous other kinds of antioxidants, sterically hindered phenols among them.

U.S. Pat. No. 3,979,180 describes the stabilization of low density polyethylene and mineral-filled ethylene vinyl acetate copolymers employing a combination of a sterically hindered phenol and/or a substituted diphenylamine of the structure Ar-NH-Ar' where Ar and Ar' are each phenyl, naphthol, substituted phenyl and naphthol including alkyl substituents of 1 to 20 carbon atoms, and halogen, a metal organic thiophosphorus compound and a trace amount of a transition metal salt.

U.S. Pat. No. 4,341,677 describes oil-in-water emulsions of antioxidants useful for treating fibrous reinforcements, such as glass fibers, to increase the protection of such fiber reinforced polymeric materials as polyolefins, polyurethanes, polyamides, polyesters, polycarbonates, polyacetals, polystyrene, and styrene copolymers against chemical degradation. The emulsions are based on hindered phenols, such as octadecyl-3-(3', 5-di-t-butyl-4'-hydroxyphenyl)propionate (IRGANOX 1076, Ciba Geigy) and/or diarylamines, such as NAUGARD 445.

U.S. Pat. No. 4,420,579 describes antioxidant compositions for polyolefins based on coordination complexes of nickel thiobis(alkylphenolates) with hydroxy-substituted ligands in combination with co-additives, such as diarylamines and/or hindered phenols.

U.S. Pat. No. 4,440,671 describes mixtures of hydrocarbon- substituted diphenylamines, for example, a liquid diphenylamine alkylated with styrene (WINGSTAY 29, Goodyear Tire and Rubber Company) and high molecular weight polyethylene glycols as water-tree retardant compositions for polyethylenes. The compositions can, optionally, contain antioxidants, such as sterically hindered phenols and amines, polymerized 2,2,4-tetramethylhydroquinoline, 4,4'-thio-bis-(6-t-butyl-3-methylphenol), thiodiethylenebis-(3,5-di-t-butyl-4-hydroxy hydrocinnamate), distearylhiodipropionate, and the like.

U.S. Pat. No. 5,047,530 discloses tris(N-alkyl-p-phenylenediamino)-1,3,5-triazine compounds useful as antiozonants for unsaturated high polymers. The compounds can be prepared by reacting N-alkylphenylenediamine with a cyanuric halide.

U.S. Pat. No. 5,120,844 discloses tris-substituted 1,3,5-triazine compounds having at least one (N-alkyl-p-phenylenediamino)group on the triazine ring. The preferred compositions are tri-substituted with the alkyl p-phenylenediamino group. The preferred compounds can be prepared by reacting N-alkylphenylenediamine with a cyanuric halide.

Japanese patent publication Number 1984-98148 teaches the discoloration inhibition of cross-linked polyolefins using 4,4'-bis-(2,2'-dimethylbenzyl) diphenylamine with optional antioxidants that are liquid at room temperature such as: 4,4'-thio-bis(6-t-butyl-3-methylphenol); dilauryl dithiopropionate; 2,2-thio[diethyl bis-3-(3,5 diethyl-t-butyl-4-hydroxyphenyl)]propionate. These polyolefins necessarily contain cross-linking agents such as the well-known organic peroxides.

SUMMARY OF THE INVENTION

The present invention relates to compounds having both aromatic amine and hindered phenol functionalities, compositions containing such compounds, and their use as stabilizers for organic materials.

More particularly, the present invention relates to a compound of the general formula:

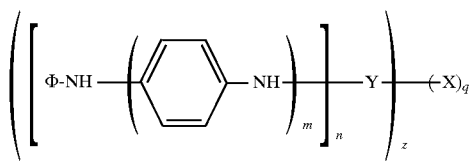

wherein:

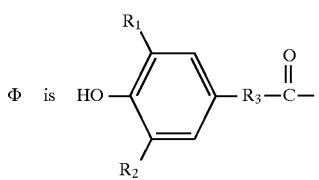

$R_1$ and $R_2$ are independently selected from the group consisting of hydrogen, substituted or unsubstituted aryl, and substituted or unsubstituted alkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1.

In another aspect, the present invention relates to a stabilizer for organic materials comprising a compound of the general formula:

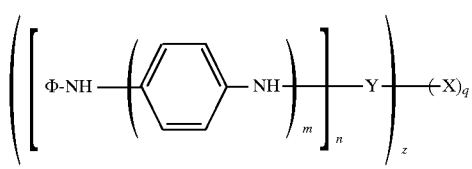

wherein:

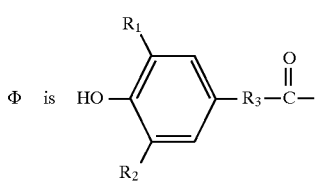

$R_1$ and $R_2$ are independently selected from the group consisting of hydrogen, substituted or unsubstituted aryl, and substituted or unsubstituted alkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1.

In still another aspect, the present invention relates to a method for stabilizing organic materials comprising adding to said materials at least one stabilizer comprising a compound of the general formula:

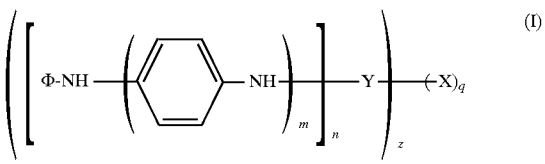

wherein:

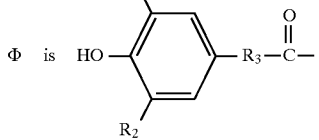

$R_1$ and $R_2$ are independently selected from the group consisting of hydrogen, substituted or unsubstituted aryl, and substituted or unsubstituted alkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1.

DESCRIPTION OF THE PREFERRED EMBODIMENTS

As stated above, the dual functional stabilizers of the present invention are of the general formula:

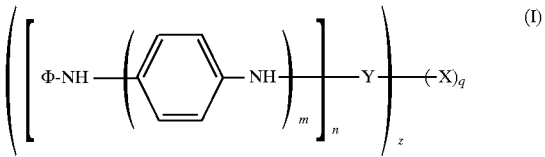

wherein:

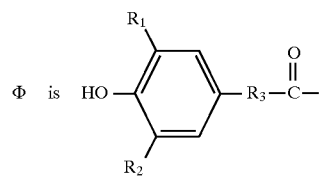

$R_1$ and $R_2$ are independently selected from the group consisting of hydrogen, substituted or unsubstituted aryl, and substituted or unsubstituted alkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1.

Thus, $R_1$ and $R_2$ in Φ of formula I can be the same or different and can be hydrogen, or an alkyl, functionalized alkyl, or aralkyl group of 1 to 20 carbon atoms. Where $R_1$ and/or $R_2$ are alkyl, they can, for example, be methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, or isomers thereof, for example, isopropyl, isobutyl, sec-butyl, tert-butyl, 2-ethylhexyl, and the like.

It is noted here that any use of the term "alkyl" in the context of a starting material or the final compounds of this invention is deemed to include cycloalkyl and alkyl substituted cycloalkyl structures as well, for example, cyclopentyl, cyclohexyl, 4-methylcyclohexyl, and the like.

Additionally, where $R_1$ and/or $R_2$ are alkyl, the alkyl group can be mono- or poly-substituted with, for example, functional groups or aryl groups. Such functional groups include, for example, halides, hydroxyl groups, aldehyde groups, carboxyl groups, sulfonyl groups, sulfoxy groups, thiol groups, amino groups, amido groups, and the like, either singly or in admixture. Aryl substituents include, for example, phenyl, naphthyl, biphenyl, azulenyl, anthracenyl, phenanthrenyl, and the like, which substituents may, also, be substituted to form, for example, tolyl groups, xylyl groups, anilinyl groups, and the like. Similarly, where $R_1$ and/or $R_2$ are aryl, they can be, for example, phenyl, naphthyl, biphenyl, azulenyl, anthracenyl, phenanthrenyl, and the like, which substituents may, also, be substituted to form, for example, tolyl groups, xylyl groups, anilinyl groups, and the like. It is preferred that at least one of $R_1$ and $R_2$ be tert-butyl and more preferred that they both be tert-butyl.

$R_3$ in Φ of formula I is an alkylene group of 1 to 10 carbon atoms, for example, methylene, ethylene, propylene, butylene, pentylene, hexylene, heptylene, octylene, nonylene, decylene, and isomers thereof, i.e., they can be unbranched or branched, for example, isopropylene, isobutylene, 2-ethylhexylene, and the like. It is preferred that $R_3$ be an unbranched alkylene group and more preferred that it be ethylene.

In formula I, $(X)_q$ refers to a moiety that may or may not be present. That is to say, if q is 0, X is not present; if q is any of 1 through 8, 1 through 8 X's will correspondingly be present. Those skilled in the art will understand that when X is present, z necessarily must be 2, and X then forms a link or links between the two Y's. As an example, where z and q are both 2, the formula for the resulting compound of the invention will be:

X in formula I can be carbon, nitrogen, oxygen, sulfur, or silicon. Where q is more than 1, the several X's can be the same or different. Those skilled in the art will understand that the carbon, nitrogen, oxygen, sulfur, or silicon referred to represent only those atoms that are the links joining the two Y's and that such additional atoms or bonds as may be necessary to satisfy the valence requirements of the chain atoms will also be present. For example, X could be carbon substituted with an oxygen atom to form a carbonyl group, or, where q is 2 and X is carbon, the structure could be . . . Y—$CH_2$—$CH_2$—Y . . . Another example would be . . . Y—CH═CH—Y . . . Additional possibilities will be readily apparent to those of ordinary skill.

Y, in formula I, is an aromatic group, which can be substituted or unsubstituted. It is preferred that Y be phenyl, naphthyl, biphenyl, azulenyl, anthracenyl, or phenanthrenyl and more preferred that it be phenyl. Where two Y's are present in the compounds of the invention, i.e., where z is 2, they can be the same or different, but it is preferred that they be the same. Additionally, when, and only when, z and m are both 1, Y can also be Φ.

In formula I, n is an integer of 1 to 10. It will be understood that the maximum value for n will be dependent upon the identity of the group chosen as Y. That is, the moiety included within the square brackets in formula I can be attached to any and all of the carbon atoms available in the aromatic group that is Y. Therefore, if Y is phenyl and has no other groups attached to it, Y will have six available carbon atoms, and the maximum value of n would be 6. On the other hand, if Y is biphenyl and has no other groups attached to it, Y will have ten available carbon atoms, and the maximum value of n would be 10. It is preferred that n be an integer from 1 to 6, more preferably from 1 to 3, and most preferably 1.

The preferred compounds of the present invention are N-(4'-anilinophenyl)-3-(3",5"-di-t-butyl-4"-hydroxyphenyl) propionamide; N-{p-[(1',4'-dimethylpentyl)amino]phenyl}-3-(3",5"-di-t-butyl-4"-hydroxyphenyl)propionamide; N,N'-phenylene-bis[3-(3",5"-di-t-butyl-4"-hydroxyphenyl) propionamide].

The compounds of this invention can be used as either partial or complete replacements for the hindered phenol and/or amine antioxidants that are currently in use. They can also be used in combination with each other or with other additives typically found in organic materials.

When employed as stabilizers, the compounds of the present invention act as antioxidants and/or antiozonants for, inter alia, plastic materials, rubbers, lubricating oils, and petroleum fuels.

The plastic materials can be a thermoplastic polyolefin, such as polyethylene or polypropylene; polystyrenes; polyvinylhalides; or other thermoplastic resins, including engineering thermoplastics. Engineering thermoplastics include resins such as polyamides, polyesters, polyacetals, polyphenyleneoxides, polyphenylenesulfides, aliphatic polyketone copolymers or terpolymers, poly(ethersulfones), polycarbonates, liquid crystalline polymers, poly (etheretherketones), and poly(arylates).

Rubbers include highly unsaturated polymers such as natural or synthetic elastomers, for example, cis-

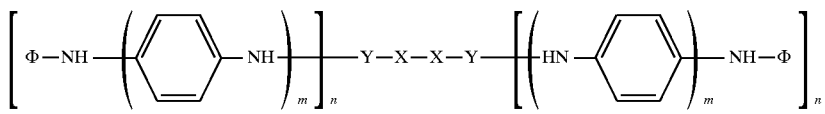

polyisoprene, polybutadiene, poly(styrene-butadiene), polychloroprene, polyacrylonitrile, and the like, as well as elastomers having lesser unsaturation such as EPDM, EPR, and butyl or halogenated butyl rubbers.

Lubricating oils can include lubrication oil, transmission oils, motor oils, and greases. Petroleum fuels and organic liquids can be gasoline, diesel fuel, or jet fuel.

Plastic Materials

The stabilization of polyethylene resins, both cross-linked and non-cross-linked, is extremely important in particular applications. Particularly, long-term serviceability is important in the jacketing for wire and cable where the wiring must maintain its stability over very long periods of time, such as 20 to 30 years or longer, in both indoor and outdoor applications. The ability to stabilize polymers such as linear low density polyethylene against long-term degradation is an important step forward in technology.

The thermoplastic polyolefins that can be stabilized against degradation employing the compounds of the present invention include homopolymers derived from mono- and di-ethylenically unsaturated hydrocarbon monomers of $C_3$ and above such as polypropylene, polyisobutylene, polymethylbutene-1, polymethylpentene-1, polybutene-1, polystyrene, polyisobutylene, and the like; copolymers derived from two or more monomers such as ethylene-propylene copolymers having at least a majority of propylene, propylene-butene-1 copolymers, propylene-isobutylene copolymers, and blends of a majority of polypropylene with a minority of polyethylene, polypropylene and polybutene-1, and polypropylene and polyisobutylene.

The foregoing polyolefin homopolymers, copolymers, and blends thereof can be combined with minor amounts by weight, i.e., less than about 50 weight percent and preferably less than about 20 weight percent, of one or more compatible or compatibilized polymers other than those mentioned, for example, polyvinyl halides, chlorinated polyolefins, polyesters, polyamides, polyacrylates, and the like.

The amount of the stabilizers of the present invention incorporated into the foregoing polyolefins will, at a minimum, be that required to impart a significant level of stability against oxidative degradation. In general, such amounts can vary from about 0.01 to about 5.0, and preferably from about 0.1 to about 0.5, weight percent of polyolefin homopolymer, copolymer, or polyolefin blend. Although amounts of the stabilizer in excess of about 5 weight percent can be employed, such amounts may have a deleterious effect on the physical and mechanical properties of the polyolefin substrate, in which case they should ordinarily be avoided.

The procedures employed to incorporate the stabilizers into the polyolefin are not critical and, in general, follow any of the known procedures for incorporating additives in polyolefin resins. For example, these materials can be introduced into the polyolefin and homogeneously distributed throughout the polymer by milling, extrusion blending, or some other mechanical working procedure. The stabilizer can be added to the polyolefin by way of a preconcentrate or in a carrier system, for example, in a suitable solvent or co-solvent.

Following common practice, other additives can be introduced into the polyolefin prior to, during and/or following addition of the stabilizer. Such additives include other stabilizers, colorants, reinforcements, fillers, antistatic agents, lubricants, plasticizers, and the like, present in their customary amounts.

Rubbers

The compounds of the invention can be advantageously utilized as antiozonants to protect highly unsaturated polymers such as natural or synthetic elastomers. Representative of the highly unsaturated polymers that can be employed in the practice of this invention are diene elastomers. Such elastomers will typically possess an iodine number of between about 100 and about 250, although highly unsaturated rubbers having a higher or a lower (for example, of 50–100) iodine number can also be employed. Illustrative of the diene elastomers that can be utilized are polymers based on conjugated dienes such as 1,3-butadiene; 2-methyl-1,3-butadiene; 1,3-pentadiene; 2,3-dimethyl-1,3-butadiene; and the like, as well as copolymers of such conjugated dienes with monomers such as styrene, alpha-methylstyrene, acrylonitrile, methacrylonitrile, methyl acrylate, ethyl acrylate, methyl methacrylate, ethyl methacrylate, vinyl acetate, and the like. Preferred highly unsaturated rubbers include natural rubber, cis-polyisoprene, polybutadiene, poly(styrene-butadiene), polychloroprene, and poly(acrylonitrile-butadiene). Moreover, mixtures of two or more highly unsaturated rubbers with elastomers having lesser unsaturation such as EPDM, EPR, butyl or halogenated butyl rubbers are also within the contemplation of the invention.

The novel compounds of the invention can be used in combination with other antiozonants and with waxes that are commonly used to protect against static attack. The other antiozonants that can be utilized include any of the commonly recognized paraphenylenediamine class of materials: N-phenyl-N'-(1,3-dimethylbutyl)-p-phenylenediamine; N-phenyl-N'-isopropyl-p-phenylenediamine; N-phenyl-N'-(1-methylheptyl)-p-phenylenediamine; N-phenyl-N'-cyclohexyl-p-phenylenediamine; mixed diaryl-p-phenylenediamines; N,N'diphenyl-p-phenylenediamine; N,N'di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine; N-phenyl-N'-alkyl-p-phenylenediamine; 6-ethoxy- 1,2-dihydro-2,2,4-trimethylquinoline; nickel dibutyl dithiocarbamate; and the like.

The highly unsaturated polymers to be protected can be formulated in a conventional manner with the many usual compounding ingredients, for example, vulcanizing agents, accelerators, activators, retarders, antiozonants, antioxidants, plasticizing oils and softeners, fillers, reinforcing pigments, and carbon blacks.

The novel compounds of the invention can be added to an unsaturated polymer at a level of 0.1 to about 10 parts by weight per hundred parts by weight of rubber hydrocarbon (hereinafter PHR). For these purposes, the polymer is assumed to be a natural or synthetic rubber. A more preferred addition level is about one to about six parts PHR. The most preferred level is from about two to about four parts PHR. When the compounds of the invention are used in combination with other antiozonants such as the p-phenylenediamine class of materials, they can be added in a blend that totals to the ranges specified above. The compounds of the invention can be blended with the other antiozonants at ratios ranging from 1:3 to 3:1. More preferred is a ratio range of 2:3 to 3:2. These ratios are meant to indicate the percentages are 40:60 to 60:40 where in all cases the compounds of the present invention are the first number of each ratio. It should be noted that in certain applications and with certain other antiozonants, the PHR ranges of antiozonant listed above may be varied in order to obtain the optimal protection. Reasonable experimentation can be undertaken in order to optimize the ratios and overall levels of the blend when the compounds of the invention are blended with other antioxidants and antiozonants that are known in the art.

The compounds of the invention can be used to good advantage with antioxidants and antiozonants of the prior art in blends to enhance particular properties. While the compounds of the invention have been described above as antiozonants when used in rubber formulations, it is clear that the materials can also function as antioxidants for rubber, thus providing protection against oxidative degradation as well as ozone protection. It is noted that when used as an antioxidant, the levels are typically much lower per hundred parts of rubber hydrocarbon than when antiozonant protection is required.

The compounds of the invention can be advantageously used in a tire as a component of any or all of the thermosetting rubber-containing portions of the tire. These include the tread, sidewall, and carcass portions of a truck, passenger, or off-road vehicle tire that also contain many different reinforcing layers therein. These components typically contain more than one thermosetting rubber polymer in a blend that must be protected from ozone degradation, as well as oxidative attack.

Methods of incorporating these compounds into the tire are conventional and well known. These compounds improve the scorch safety of the rubber stock in which they are incorporated compared to conventional p-phenylenediamines.

Unsaturated polymers can be optionally protected against both oxidative and ozone degradation by blending the compounds of the invention with conventional antioxidants. Many classes of phenolics, amines, etc., function as antioxidants. The *Index of Commercial Antioxidants and Antiozonants*, 3rd Edition, published by The Goodyear Tire and Rubber Company lists materials commonly viewed as materials having antioxidant properties, and is incorporated herein by reference. Representative classes of such antioxidant materials are sterically hindered phenols, alkyl-substituted diphenylamines, aryl-substituted diphenylamines, aralkyl-substituted diphenylamines, naphthylamines, reaction products of a diarylamine and a ketone, mono-phenols, bisphenols, polyphenols, hydroquinone derivatives, and polymerized quinolines. The antioxidant system can contain one or more of these materials. Optimal levels of addition (PHR) for the antioxidants can be easily determined through routine experimentation and can vary widely depending upon the end use.

EXAMPLES

General Synthesis of Stabilizers

Example 1

N-(4'-Anillnophenyl)-3-(3",5"-di-t-butyl-4"-hydroxyphenyl)propionamide

N-(4'-Anilinophenyl)-3-(3",5"-di-t-butyl-4"-hydroxyphenyl)propionamide (hereinafter, Stabilizer A) was synthesized by charging a one-liter, four-necked round-bottom flask with methyl 3-(3,5-di-t-butyl-4-hydroxyphenyl)propionate (Reagent 1) and usually a slight excess (5 to 10 percent) of 4-aminodiphenylamine (Reagent 2). Reagent 1 can be prepared as the Michael addition reaction product of 2,6-di-t-butylphenol with methyl acrylate. Reagent 2 is commercially available from Aldrich Chemical Company and Uniroyal Chemical Company. The ratio of Reagent 1 to Reagent 2 can vary from 1.5 to 0.67. A preferable ratio of Reagent 1 to Reagent 2 is 1.2 to 0.84, and the most preferred ratio of Reagent 1 to Reagent 2 is 1.0 to 0.91. The reaction vessel itself was equipped with a paddle stirrer, nitrogen subsurface fitted sparger, a thermocouple, and gas outlet tube leading to a cold trap. The reaction vessel was heated between 180 and 250° C. and preferably between 200 and 230° C., and most preferably at 230° C. The reaction was monitored by High Performance Liquid Chromatography (HPLC) until the product yield was maximized - usually 2 to 16 hours, and more preferably 4 to 8 hours. Upon completion of the reaction, the sparger was removed, the reaction was cooled to 120° C. and an organic solvent mixture, usually a mixture of a saturated aliphatic solvent and an unsaturated aromatic solvent such as octane and toluene, was added over one hour. Crystallization of the product in either octane and toluene was completed, but the crystallization purity or yield usually suffered. The crystallization solution was held at 115° C. and slowly cooled until crystallization was completed, usually to between 25 and 90° C. The product was filtered, washed with octane, and dried. This process yields a light gray product between 65 percent to 85 percent yield. The purified product melted between 139 and 144° C., though crude or less purified product will melt between 110 and 140° C. $^1$H NMR(CDCl$_3$, 300 MHz): 1.44(s, 18H), 2.63(t,J=7.8 Hz, 2H), 2.99(t, J=7.8 Hz, 2H), 5.12(s, 1H), 5.69(s, broad, 1H), 6.91–7.35(m, 11H). $^{13}$C NMR(CDCl$_3$, 75 MHz): 170.7, 152.3, 143.6, 139.5, 136.2, 131.6, 131.2, 129.4, 121.5, 120.6, 119.0, 117.1, 40.1, 34.4, 31.9, 30.4. IR(cm$^{-1}$): 3620, 3430, 3272, 2955, 1649. Elemental Analysis. Calculated: C 78.34 percent, H 8.16 percent, N 6.30 percent, O 7.20 percent. Found: C 78.53 percent, H 8.34 percent, N 6.27 percent, O 6.49 percent.

Example 2

Reagent 2 in Excess

The synthesis of Stabilizer A described in Example 1 is carried out using 11.68 g of Reagent 1 (0.04 mole) and 8.1 g of Reagent 2 (0.044 mole), i.e., an excess amount of Reagent 2 is used. A product of the kind described in Example 1 is obtained.

Example 3

Reagent 1 in Excess

The synthesis of Stabilizer A described in Example 1 is carried out using 17.52 g of Reagent 1 (0.06 mole) and 7.36 g of Reagent 2 (0.04 mole), i.e., an excess amount of Reagent 1 is used. A product of the kind described in Example 1 is obtained.

Example 4

N-{p-[(1',4'-Dimethylpentyl)amino]phenyl}-3-(3",5"-di-t-butyl-4"-hydroxyphenyl) propionamide N-{p-[(1',4'-Dimethylpentyl)amino]phenyl}-3-(3",5"-di-t-butyl-4"-hydroxyphenyl) propionamide (Stabilizer B). Into a 500 ml four-necked round-bottomed flask equipped with a thermocouple, a mechanical stirrer, a condenser, and a Stark-Dean trap with condenser, was placed a quantity of 73 g (0.25 mole) of Reagent 1, and 61.8 g (0.3 mole) of N-(1,4-dimethylpentyl)-p-phenylenediamine. (N-(1,4-dimethylpentyl)-p-phenylenediamine can be made by the condensation of p-nitroaniline with methyl isoamyl ketone, followed by hydrogenation.) Under a blanket of nitrogen, the mixture was heated to 230° C. for six hours. The reaction was monitored by HPLC to observe the disappearance of the starting materials and the formation of the title compound. Upon cooling down to 100° C., 200 g of toluene was added. The toluene solution was extracted with dilute hydrochloric acid, followed by washing with a sodium carbonate solution and water. The solvent was removed by vacuum stripping. The resulting product (116 g) was an oil. Relative area HPLC analysis (@280 nm detection) of this product was 87 percent.

Example 5

N,N'-Phenylene-bis[3-(3",5"-di-t-butyl-4"-hydroxyphenyl)propionamide]

N,N'-Phenylene-bis[3-(3",5"-di-t-butyl-4"-hydroxyphenyl)propionamide](Stabilizer C). A mixture of Reagent 1 (73.3 g, 0.26 mole) and p-phenylenediamine (10.8 g, 0.1 mole) was placed in a three-neck round-bottom flask, equipped with a Stark-Dean receiver, a thermocouple, and a gas inlet. The reaction mixture was heated nine hours at 230° C. under $N_2$, with agitation. The resulting product mixture was recrystallized from acetonitrile. The purified material, N,N'-phenylene-bis[3-(3",5"-di-t-butyl-4"-hydroxyphenyl) propionamide], has a melting point in the range 238–245° C.

Oxidative Induction Times

Circular discs are cut from 0.25 mm films of the material to be tested and placed in aluminum pans for use in a Perkin-Elmer DSC-2C type differential scanning calorimeter (DSC). The test chamber of the DSC calorimeter is purged with nitrogen during conditioning to an isocratic temperature of 200° C. followed by an immediate change to oxygen at a flow rate of 20 cc's per minute to induce thermal oxidative degradation. Oxidative Induction Time (OIT) is the time span in minutes between reaching an isocratic temperature of 200° C. when the oxygen environment is introduced and the time at which the DSC detects the onset of oxidation.

Example 6

Stabilizer for Plastics

The antioxidant properties of the novel product in a fully formulated plastic were determined in the Oxidation Induction Time (OIT) test under ASTM D3895 conditions at 200° C. The plastic formulation contained 0.2 percent of the dual functional antioxidant Stabilizer A, 2.5 percent of a carbon black, and 97.3 percent of linear low density polyethylene (LLDPE). The OIT results of various state of the art antioxidants are included in Table 1. In the OIT test, a longer OIT value indicates better oxidative stability of the formulation. The results in Table 1 are the average of at least three tests.

TABLE 1

OIT RESULTS

| Compound | OIT (min) |
|---|---|
| Stabilizer A | 124 |
| Naugard Super Q | 50 |
| Naugard A | 39 |

Naugard Super Q is a polymerized 2,2,4-trimethyl-1,2-dihydroquinoline having a narrower molecular weight distribution than Naugard Q, infra.

Naugard A is a condensation reaction product of diphenylamine and acetone, commercially available from Uniroyal Chemical. It can be prepared in accordance with the conditions described in U.S. Pat. No. 2,562,802. The commercial product is supplied as a light tan-green powder or as greenish brown flakes and has a melt range of 85 to 95° C.

Example 7

Stabilizer for Rubber

Evaluation of Stabilizer A in a Truck NR/BR Carcass-Compound: Unaged physical properties for Stabilizer A show a promising similarity to the Naugard Q and Novazone AS controls. Aged physical results further show a slight superiority in nearly all percent retention values for Stabilizer A versus the controls.

Samples are formulated in two steps. In the first step, a masterbatch is prepared and in the second step, the masterbatch is further compounded to form three samples, A, B, and C. See Table 2.

TABLE 2

| Ingredients | A | B | C |
|---|---|---|---|
| Natural Rubber | 70 | 70 | 70 |
| Cis-Butadiene Rubber | 30 | 30 | 30 |
| Black N-660 | 50 | 50 | 50 |
| Zinc oxide | 4 | 4 | 4 |
| Stearic Acid | 1.5 | 1.5 | 1.5 |
| Naphthenic Oil | 7.5 | 7.5 | 7.5 |
| Benzothiazole disulfide | 0.6 | 0.6 | 0.6 |
| Insoluble Sulfur, 80% in oil | 3.2 | 3.2 | 3.2 |
| Naugard Q | 2.0 | | |
| Novazone AS | | 2.0 | |
| Stabilizer A | | | 2.0 |
| Total, phr | 168.8 | 168.8 | 168.8 |

Novazone AS is a mixture of N,N'-diaryl p-phenylenediamines and is commercially available from Uniroyal Chemical Company.

TABLE 3

| | Unaged Physical Properties | |
|---|---|---|
| Sample | Tensile Strength | Elongation (% at break) |
| A | 2080 psi | 540 |
| B | 2290 psi | 550 |
| C | 2020 psi | 540 |

TABLE 4

| Physical Properties - Aged 3 Days at 100° C. | | | | |
|---|---|---|---|---|
| 1 | 2 | 3 | 4 | 5 |
| A | 1680 | 81 | 270 | 50 |
| B | 1720 | 75 | 270 | 49 |
| C | 1860 | 92 | 320 | 59 |

1—Sample
2—Tensile Strength (in psi)
3—Percent Retention (Tensile Strength)
4—Elongation (percent at break)
5—Percent Retention (Elongation)

The Tensile Strength and Elongation properties were measured according to ASTM #D412. The test specimens were in the shape of dumbbells. The Tensile Strength and Elongation properties of the test specimens were measured before aging and also after hot air aging at 100° C. for three days.

The White Lacquer Dip Test uses ASTM #D1148(09.0) and D925(09.01), which are incorporated herein by reference. The test formulation is compounded, mixed, and cured into flat test sheets for subsequent analysis of discoloration and staining characteristics. The specific testing is conducted in accordance with ASTM-D925-83 Method C. The Method C judges the degree of staining tendency of material by determining the amount of discoloration that occurs from the substrate material through a white lacquer coating that has been placed on the test sample. Once the test specimen is mixed and cured, it is coated with a veneer of white lacquer in accordance with the ASTM-D925 procedure. It is then exposed to a sunlamp light source in a suitable test chamber for a specified period of time. The Hunter Lab™ Colorimeter test apparatus is utilized to objectively determine the change in the color of the white lacquer during a 24-hour exposure to a UV source. ASTM D2244-79, entitled *Color Differences of Opaque Materials*, reports a number of characteristics by the standard difference letters a, b, and L. The L color scale is a scale from 0 to 100 with a 0 value being totally black and a 100 value being pure white. Therefore, the higher the L value, the whiter the sample. The results of the white lacquer dip test are shown in Table 5.

TABLE 5

White Lacquer Dip

| Sample | Hunter L Color | | Hunter a Color | | Hunter b Color | |
|---|---|---|---|---|---|---|
| | Unaged | Aged | Unaged | Aged | Unaged | Aged |
| A | 84.59 | 82.82 | −1.75 | −2.50 | 0.91 | 6.21 |
| B | 83.64 | 59.61 | −1.95 | 3.35 | 3.00 | 12.95 |
| C | 82.94 | 77.82 | −2.02 | −0.74 | 3.84 | 10.90 |

L—a finite scale (0–100) that determines the colors black (0) and white (100).

a—a relative scale that determines the colors green (negative) and red (positive).

b—a relative scale that determines the colors blue (negative) and yellow (positive).

The unaged white lacquer dip properties of stabilizer A are shown to be equivalent to the Naugard Q and Novazone AS controls. Upon aging 24 hours under a UV lamp, results indicate the non-staining characteristics of Stabilizer A to be close (slightly inferior) to Naugard Q, but superior to Novazone AS.

Results of this set of experiments conclude that the antioxidant properties of Stabilizer A is superior to Novazone AS and Naugard Q. In addition, the lacquer dip test showed Stabilizer A is nearly non-staining, comparable to Naugard Q.

Example 8

Stabilizer for Lubricating Oils

Stabilizer A was tested in two different Lubrizol lubricating oils using a Bulk Oxidation Test (BOT). The BOT test involves dissolving the additive (0.6 percent in Diesel motor oil and 0.5 percent in Automatic Transmission Fluid{ATF} oil) in the oil. The oil is heated (150° C. for Diesel motor oil and 160° C. for ATF oil) and then oxygen is bubbled (1 L/min) through the oil. The kinematic viscosity (K.V.) is then measured over time until this value reaches 200 percent of its original value. In this test, a longer time corresponds to a better stabilizing additive. The two different oils were Lubrizol's Diesel 118359 and ATF 118160. A summary of the test conditions and results is given in Table 6. The test results show that Stabilizer A increases the oxidative resistance of both the Diesel and ATF oils, as compared to the resistance of the oils without a stabilizer.

TABLE 6

| Oil Sample | Antioxidant | BOT Temp. | Time to 200% K.V. Increase |
|---|---|---|---|
| Diesel 118359 | None | 150° C. | 24 hours |
| Diesel 118359 | Stabilizer A | 150° C. | 48 hours |
| ATF 118160 | None | 160° C. | 48 hours |
| ATF 118160 | Stabilizer A | 160° C. | 96 hours |

In view of the many changes and modifications that can be made without departing from principles underlying the invention, reference should be made to the appended claims for an understanding of the scope of the protection afforded the invention.

What is claimed is:

1. A compound of the general formula:

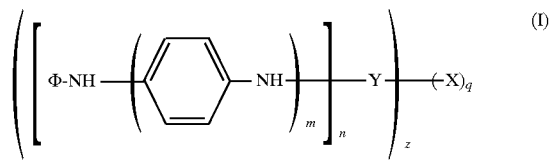

wherein:

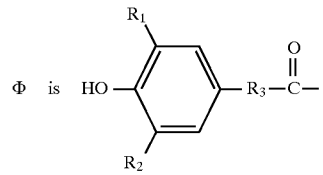

$R_1$ and $R_2$ are independently selected from the group consisting of hydrogen, unsubstituted aryl, tolyl, xylyl, anilinyl, and alkyl, functionalized alkyl or aralkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1 and can be phenyl or alkyl substituted phenyl only when at least one of m and q is not 0.

2. The compound of claim 1 wherein $R_1$ and $R_2$ are unsubstituted alkyl of 1 to 20 carbon atoms.

3. The compound of claim 2 wherein $R_1$ and $R_2$ are the same.

4. The compound of claim 3 wherein $R_1$ and $R_2$ are tert-butyl.

5. The compound of claim 1 wherein $R_3$ is an unbranched alkylene of 1 to 10 carbon atoms.

6. The compound of claim 5 wherein $R_3$ is propylene.

7. The compound of claim 1 wherein Y is aromatic.

8. The compound of claim 7 wherein Y is phenyl.

9. The compound of claim 1 wherein said compound is N-(4'-anilinophenyl)-3-(3",5"-di-t-butyl-4"-hydroxyphenyl) propionamide.

10. The compound of claim 1 wherein said compound is N-{p-[(1',4'-dimethylpentyl) amino]phenyl}-3-(3",5"-di-t-butyl-4"-hydroxyphenyl)propionamide.

11. The compound of claim 1 wherein said compound is N,N'-phenylene-bis[3-(3",5"-di-t-butyl-4"-hydroxyphenyl)propionamide].

12. A stabilizer for organic materials comprising a compound of the general formula:

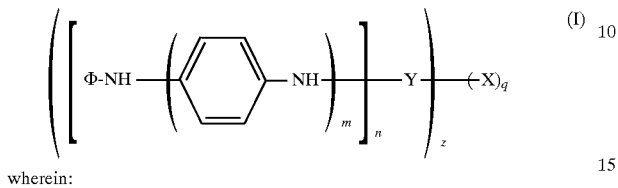

wherein:

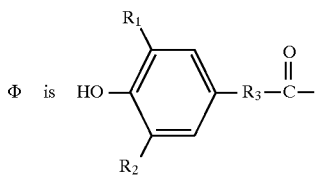

$R_1$ and $R_2$ are independently selected from the group consisting of hydrogen, unsubstituted aryl, tolyl, xylyl, anilinyl, and alkyl, functionalized alkyl, or aralkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1 and can be phenyl or alkyl substituted phenyl only when at least one of m and q is not 0.

13. The stabilizer of claim 12 wherein $R_1$ and $R_2$ are unsubstituted alkyl of 1 to 20 carbon atoms.

14. The stabilizer of claim 13 wherein $R_1$ and $R_2$ are the same.

15. The stabilizer of claim 14 wherein $R_1$ and $R_2$ are tert-butyl.

16. The stabilizer of claim 12 wherein $R_3$ is an unbranched alkylene of 1 to 10 carbon atoms.

17. The stabilizer of claim 16 wherein $R_3$ is propylene.

18. The stabilizer of claim 12 wherein Y is aromatic.

19. The stabilizer of claim 18 wherein Y is phenyl.

20. The stabilizer of claim 12 wherein the compound is N-(4'-anilinophenyl)-3-(3",5"-di-t-butyl-4"-hydroxyphenyl)propionamide.

21. The stabilizer of claim 12 wherein the compound is N-{p-[(1',4'-dimethylpentyl) amino]phenyl}-3-(3",5"-di-t-butyl-4"-hydroxyphenyl)propionamide.

22. The stabilizer of claim 12 wherein the compound is N,N'-phenylene-bis[3-(3",5"-di-t-butyl-4"-hydroxyphenyl)propionamide].

23. A method for stabilizing organic materials comprising adding to said materials at least one stabilizer comprising a compound of the general formula:

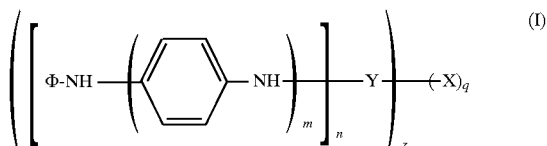

wherein:

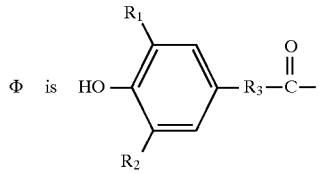

$R_1$ and $R_2$ are independently selected from the group consisting of hydrogen, unsubstituted aryl, tolyl, xylyl, anilinyl, and alkyl, functionalized alkyl, or aralkyl of 1 to 20 carbon atoms;

$R_3$ is alkylene of 1 to 10 carbon atoms;

m is 0 or 1;

n is an integer of 1 to 10;

q is an integer of 0 to 8;

z is 1 or 2, provided that, when q is 0, z must be 1;

X represents the links of a chain q links in length, said links being selected from the group consisting of carbon, nitrogen, oxygen, sulfur, silicon, and mixtures thereof; and Y is an aromatic group or Φ, provided that Y can be Φ only when q is 0 and m is 1 and can be phenyl or alkyl substituted phenyl only when at least one of m and q is not 0.

24. The method of claim 23 wherein $R_1$ and $R_2$ are unsubstituted alkyl of 1 to 20 carbon atoms.

25. The method of claim 24 wherein $R_1$ and $R_2$ are the same.

26. The method of claim 25 wherein $R_1$ and $R_2$ are tert-butyl.

27. The method of claim 23 wherein $R_3$ is an unbranched alkylene of 1 to 10 carbon atoms.

28. The method of claim 27 wherein $R_3$ is propylene.

29. The method of claim 23 wherein Y is aromatic.

30. The method of claim 29 wherein Y is phenyl.

31. The method of claim 23 wherein the compound is N-(4'-anilinophenyl)-3-(3",5"-di-t-butyl-4"-hydroxyphenyl)propionamide.

32. The method of claim 23 wherein the compound is N-{p-[(1',4'-dimethylpentyl) amino]phenyl}-3-(3",5"-di-t-butyl-4"-hydroxyphenyl)propionamide.

33. The method of claim 23 wherein the compound is N,N'-phenylene-bis[3-(3",5"-di-t-butyl-4"-hydroxyphenyl)propionamide].

* * * * *